United States Patent [19]

Vedres et al.

[11] Patent Number: 4,810,709

[45] Date of Patent: Mar. 7, 1989

[54] NINTROVINCAMINIC ACID DERIVATIVES HAVING PHARMACEUTICAL UTILITY

[75] Inventors: Andras Vedres; Csaba Szantay; Istvan Moldvai; Bela Stefko; Dora Groo; Egon Karpati, all of Budapest; Bela Kiss, Vecses; Eva Palosi, Budapest; Miklos Riesz, Budapest; Zsolt Szombathelyi, Budapest; Laszlo Szporny, Budapest; Maria Zajer nee Balazs, Budapest, all of Hungary

[73] Assignee: Richter Gedeon Vegyeszefi Gyar R.T., Budapest, Hungary

[21] Appl. No.: 105,959

[22] Filed: Oct. 7, 1987

Related U.S. Application Data

[63] Continuation of Ser. No. 753,167, Jul. 9, 1985, abandoned.

[30] Foreign Application Priority Data

Jul. 11, 1984 [HU] Hungary .................. 2704/84

[51] Int. Cl.$^4$ .................. A61K 31/475; C07D 461/00
[52] U.S. Cl. .................. 514/283; 544/125; 544/361; 546/51
[58] Field of Search .................. 546/51; 544/125, 361; 514/237, 253, 283

[56] References Cited

U.S. PATENT DOCUMENTS

| | | | |
|---|---|---|---|
| 3,891,640 | 6/1975 | Plat et al. ............... | 546/51 X |
| 3,966,745 | 6/1976 | Giudicelli et al. ............... | 546/51 |
| 4,011,330 | 3/1977 | Giudicelli et al. ............... | 514/283 |
| 4,680,397 | 7/1987 | Keve et al. ............... | 546/51 |

FOREIGN PATENT DOCUMENTS

| | | | |
|---|---|---|---|
| 2253750 | 5/1973 | Fed. Rep. of Germany ........ | 546/51 |
| 2287227 | 6/1976 | France ............... | 546/51 |
| 2342980 | 11/1977 | France ............... | 514/283 |

OTHER PUBLICATIONS

Lewin et al., Heterocycles, vol. 14, No. 12, pp. 1915–1920, (1980).

Kisfaludy et al., Chemical Abstracts, vol. 76: 34461k, (1972).

Loerincz et al., Chemical Abstracts, vol. 79: 42726c, (1973).

Giudicelli et al., Chemical Abstracts, vol. 86: 90117w, (1977).

Molino et al., Chemical Abstracts, vol. 94: 30986j, (1981).

Primary Examiner—Donald G. Daus
Assistant Examiner—Diana G. Rivers
Attorney, Agent, or Firm—Keil & Weinkauf

[57] ABSTRACT

The invention relates to a new process for preparing novel racemic and optically active 9- or 11-nitroapovincaminic acid derivatives of the general formula (I)

(I)

wherein R stands for a —CO—X group, wherein X means a halogen atom; or for a —CO—OR$^1$ group, wherein R$^1$ means an optionally mono- or polysubstituted $C_{1-10}$ aliphatic group, a $C_{3-8}$ alicyclic group or an aromatic $C_{6-14}$ hydrocarbyl group; or for a —CO—NR$^2$R$^3$ group, wherein R$^2$ and R$^3$ are the same or different and stand for a hydrogen atom or a $C_{1-8}$ alkyl group optionally forming a saturated heterocycle together with the adjacent nitrogen atom and optionally with one or more further nitrogen atoms or other heteroatoms, and R$^3$ may also represent an amino group when R$^2$ stands for a hydrogen atom; or for a cyano group, as well as their salts and pharmaceutical preparations containing these compounds. Furthermore the invention relates to a process for preparing these compounds and preparations.

The racemic and optically active substances of the general formula (I) as well as their pharmaceutically acceptable acid addition and quaternary salts have valuable therapeutic properties, namely vasodilating, spasmolytic, antihypoxic and anticonvulsive effects.

8 Claims, No Drawings

NINTROVINCAMINIC ACID DERIVATIVES HAVING PHARMACEUTICAL UTILITY

This application is a continuation of application Ser. No. 753,167, filed on July 9, 1985, now abandoned.

The invention relates to novel 9- or 11-nitroapovincaminic acid derivatives. More particularly, the invention relates to new, racemic and optically active nitroapovincaminic acid derivatives of the formula (I)

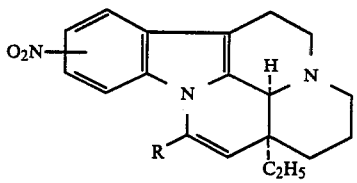

(I)

wherein r stands for a —CO—X group, wherein X means a halogen atom; or for a —CO—OR$^1$ group, wherein R$^1$ means an optically mono- or polysubstituted C$_{1-10}$ aliphatic group, a C$_{3-8}$ alicyclic group or an aromatic C$_{6-14}$ hydrocarbyl group; or for a —CO—NR$^2$R$^3$ group, wherein R$^2$ and R$^3$ are the same or different and stand for a hydrogen atom or a C$_{1-8}$ alkyl group optionally forming a saturated heterocycle together with the adjacent nitrogen atom and optionally with one or more further nitrogen atoms or other heteroatoms, and R$^3$ may also represent an amino group when R$^2$ stands for a hydrogen atom; or for a cyano group, as well as their salts and pharmaceutical preparations containing these compounds.

According to another aspect of the invention there is provided a process for the preparation of the new compounds of the formula (I) and salts thereof, which comprises (a) reacting a racemic or optically active 9- or 11-nitroapovincaminic acid derivative of the formula (II)

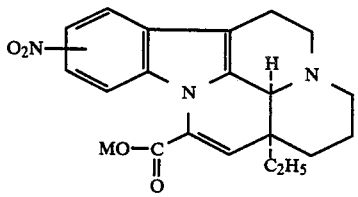

(II)

wherein M stands for a hydrogen or a metal atom or an ammonium group or, when the meaning of M is different from a metal atom, an acid addition salt of same with a compound of the general formula

R$^1$—Y wherein Y stands for a hydroxyl group or an acid residue and R$^1$ is as defined above for the general formula (I)—optionally in the presence of an inorganic base, or treating it with a halogenating agent and, if desired, reacting the thus-obtained 9- or 11-nitroapovincaminic acid derivative of the formula (I), wherein R represents a —CO—X group (wherein X stands for a halogen atom), with a nucleophilic reactant of the general formula H—OR$^1$ or H—NR$^2$R$^3$, wherein R$^1$, R$^2$ and R$^3$ are the same as defined above for the general formula (I), and, if desired, treating the thus-obtained 9- or 11-nitroapovincaminic acid derivative of the formula (I), wherein R represents a —CO—NR$^2$R$^3$ group (where both R$^2$ and R$^3$ are hydrogen atoms), with a dehydrating agent, or (b) nitrating a racemic or optically active apovincaminic acid derivative of the formula (III),

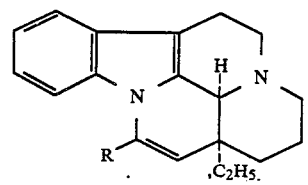

(III)

wherein R is as defined above for the formula (I), or an acid addition salt thereof, and if desired, subjecting the 9- or 11-nitroapovincaminic acid derivative of the general formula (I), wherein R represents a —CO—OR$^1$ group (wherein R$^1$ stands for C$_{1-2}$ alkyl group), obtained by using any one of the above processes, to a transesterification or amidation and/or transforming the 9- or 11-nitroapovincaminic acid derivative of the formula (I), wherein R is as defined above for formula (I), prepared by using any one of the above processes, to an acid addition salt and/or a quaternary salt and/or resolving the racemic 9- or 11-nitroapovincaminic acid of the formula (I), wherein R is as defined above for the formula (I).

In the above formulae X may be any halogen atom such as chlorine, fluorine, bromine or iodine atom. M may represent any metal atom, suitably a metal of column I or II of the periodical system, preferably an alkaline metal atom such as sodium, potassium or lithium; or an alkaline earth atom such as magnesium or calcium; or a noble metal atom such as the silver atom. Y may represent a residue of any inorganic acid, e.g. halides such as fluoride, chloride, bromide or iodide or sulphate and the like. As an aliphatic hydrocarbyl group containing 1 to 10 carbon atoms R$^1$ may represent straight or branched chain, saturated or unsaturated groups, e.g. a methyl, ethyl, n-propyl, isopropyl, n-butyl, secondary-butyl, tertiary-butyl, isobutyl, n-pentyl, isopentyl, n-hexyl, isohexyl, n-heptyl, isoheptyl, n-octyl, isooctyl, vinyl, acryl, methacryl, propenyl group or the like. As an alicyclic group R$^1$ may stand for groups containing 3 to 8 carbon atoms optionally substituted by an alkyl group such as e.g. the cyclopropyl, cyclobutyl, cyclopentyl, cyclohexyl, cycloheptyl or cyclooctyl group. As an aromatic hydrocarbyl group containing 6 to 14 carbon atoms R$^1$ may represent any monocyclic, e.g. a phenyl group; or an isolated polycyclic, e.g. diphenyl group; or a condensed ring system, e.g. a naphthyl group. As alkyl groups containing 1 to 8 carbon atoms R$^2$ and R$^3$ may represent the alkyl groups containing 1 to 8 carbon atoms, mentioned above for the R$^1$ group; R$^2$ and R$^3$ together with the adjacent nitrogen atom and optionally with one or more further nitrogen atoms or other heteroatoms may form e.g. the following saturated heterocycles: a five-membered ring containing one nitrogen atom such as pyrrolidine; a six-membered ring containing one nitrogen atom such as e.g. piperidine; a five-membered ring containing two nitrogen atoms such as e.g. imidazolidine; a six-membered ring containing two nitrogen atoms such as e.g. piperazine; a six-membered ring containing one nitrogen and one oxygen atom such as e.g. morpholine.

The substituents of the above aliphatic, alicyclic and aromatic hydrocarbyl groups may be e.g. halogen atoms, primary, secondary or tertiary amino groups, a hydroxyl group, a $C_{6-14}$ aryl group, a $C_{1-8}$ alkyl group, a $C_{1-8}$ alkoxy group, a $C_{1-8}$ alkylthio group, a trifluoromethyl group, carboxyl group, an alkoxycarbonyl group containing 1 to 8 carbon atoms, a thio, sulphinyl, sulphonyl, nitro, keto, aldehyde or cyano group as well as heteroaryl groups optionally containing the substituents mentioned above.

The heteroaryl groups may be five-, six- or seven-membered mono- or polycyclic groups containing one or more identical or different heteroatoms such as the nitrogen and/or oxygen and/or sulphur atom. Such heteroaryl groups are e.g. the pyrrolyl, furyl, thienyl, pyridyl, pyranyl, pyrazolyl, imidazolyl, pyrimidinyl, indolyl or quinolyl groups and the like.

The salts of the compounds of formula (I) may be both acid addition as well as quaternary salts. Examples of the quaternary salts are the methoiodide, methobromide, methosulphate as well as the alkyl homologues thereof containing 2 to 4 carbon atoms such as the ethoiodide and the like. The acid addition salts may be formed with inorganic acids such as the hydrohalides, hydrobromides, sulphates, phosphates and the salts of the perhalogenic acids, e.g. of the perchloric acid; on the other hand, the acid components of these salts may be organic acids such as e.g. formic, acetic, propionic, glycolic, maleic, hydroxymaleic, fumaric, tartaric, ascorbic, citric, malic, salicylic, lactic, cinnamic, benzoic, phenylacetic, p-aminobenzoic, p-hydroxybenzoic and p-aminosalicylic acid; or alkanesulphonic acids, e.g. methane- or ethanesulphonic acid or the like; or alicyclic sulphonic acids, e.g. cyclohexanesulphonic acid; arylsulphonic acids, e.g. naphthalene-, p-toluene- or p-aminobenzenesulphonic acid and the like; as well as aminoacids, e.g. aspartic, glutamic, N-acetylaspartic or N-acetylglutamic acid and the like.

Out of the derivatives of nitroapovincaminic acid, the methyl ester of 9- and 11-nitroapovincaminic acid have only been reported in the French patent specification No. 2,342,980. According to this patent specification, these compounds were prepared in two ways. According to the first method apovincamine was directly nitrated to give a mixture of the nitro isomers. The 9-nitroapovincamine was separated from this mixture of isomers by recrystallization from methanol, while 11-nitroapovincamine remained in the methanolic mother liquor and was isolated in an amorphous form after purification of the mother liquor by chromatography. According to an other method 9- and 11-nitroapovincamine, respectively, were synthetized by dehydrating 9- or 11-nitrovincamine, respectively. Anhydrous formic acid was used as dehydrating agent at a temperature of 100° C. This reaction is tedious and requires 48 or 24 hours, respectively. The purification of the end products needs chromatography in several cases.

The process of the invention, on the one hand, renders possible the preparation of a high number of novel 9- or 11-nitroapovincaminic acid derivatives, respectively, of the most varied types and, on the other hand, it shows a number of advantages in comparison to the processes of the prior art reported and cited above in the literature for preparing 9- or 11-nitroapovincamine, respectively. These advantages are as follows.

The process of the invention is extremely flexible in such a sense that the acid derivative of the general formula (I), namely the acid halides, esters, amides, hydrazides and nitriles, can in every case be prepared from the starting materials of the general formula (II) or (III), respectively, with the appropriate reactants by using the most preferable process chosen according to the physical and chemical nature of the given compounds. A further practical advantage of the process of the invention consists in that the formation of the double bond between the carbon atoms in positions 14 and 15 does not require the appropriate derivative containing the nitro group (as described in the literature cited above) since both the starting materials of the general formula (II) and (III) contain this double bond. According to the cited literature this double bond can be formed by dehydrating the appropriate vincamine derivatives but this process needs more severe reaction conditions for nitro derivatives. Consequently, the danger of side reactions is higher and thus the desired product contains more contaminations and the yield of the reaction is also diminished. Another benefit of the process of the invention is the possibility of separating the 9-nitro derivative from the 11-nitro isomer in the most suitable phase, e.g. in the earliest phase of the process, i.e. within the preparation of the starting materials.

On the reproduction of the process reported in the French specification cited above it was observed that a side product is also formed in an amount of about 30% in addition to the two isomers, i.e. the 9- and 11-nitroapovincamines mentioned above. The separation of 11-nitroapovincamine remaining in the mother-liquor is made difficult even by the presence of this side product. A further benefit of the claimed process consists in that an extremely pure product is easily separated and obtained in a high yield by using any one of the process variants.

The starting materials of the formula (II) used in the process of the invention are new compounds, the preparation of which is described in a simultaneously filed application. The principle of the preparation process is that apovincaminic acid is nitrated, whereupon the thus-obtained 9- and 11-nitroapovincaminic acids are separated from another in a simple way.

The starting materials of the formula (III) used in the process of the invention can be prepared e.g. by esterifying or amidating apovincaminic acid.

According to process (a) of the invention, in addition to the compounds of the formula (II) the salts thereof may also be used as starting materials. These salts may be on the one hand acid addition salts which can be formed by using the acids mentioned above, and on the other hand they may be metal salts or ammonium salts which can be prepared by using an inorganic base, suitably an alkaline metal hydroxide, e.g. sodium hydroxide, potassium hydroxide or ammonium hydroxide; further on, these salts may also be quaternary compounds which can be synthesized by means of e.g. an alkyl halide containing 1 to 4 carbon atoms such as methyl, ethyl and propyl chloride or methyl, ethyl and propyl bromide or iodide, or by using an alkyl sulphate containing 1 to 4 carbon atoms such as methyl or ethyl sulphate or the like.

When the meaning of M is a hydrogen atom in the starting material of general formula (II) used in the process (a) of the invention, then Y is the compound of the general formula $R^1$—Y stands suitably for a hydroxyl group, i.e. an acid is directly esterified with an alcohol. This esterification may preferably be accomplished by using an excess of the compound of general formula $R^1$—Y, wherein Y stands for a hydroxyl group and $R^1$ is as defined above, suitably under anhydrous conditions and preferably in the presence of a catalyst. This catalyst may be an organic or inorganic acid, e.g. hydrogen chloride preferably in gaseous form as well as sulphuric or p-toluenesulphonic acid and the like. A water binding agent, e.g. an appropriate molecular sieve, may also be used. This process is particularly advantageous for preparing compounds of the general formula (I) containing an R moiety which represents a —CO—$OR^1$ group where $R^1$ stands for an alkyl group containing 1 to 4 carbon atoms.

When process (a) of the invention is accomplished by using a compound of the general formula $R^1$—Y, wherein Y stands for an acid residue, then in the starting material of the general formula (II) M may represent either a hydrogen atom or a metal atom of an ammonium group. When in the compound of the general formula (II) M stands for hydrogen atom, then the process of the invention is suitably carried out in the presence of an organic base, e.g. in the presence of an alkaline metal hydroxide such as lithium, potassium or sodium hydroxide; or in the presence of an alkali carbonate such as sodium or potassium carbonate; or by using ammonium hydroxide as a base. When in the compound of the general formula (II) M stands for hydrogen atom, then the appropriate metal or ammonium salt can be formed in the reaction mixture by adding the appropriate inorganic base. Subsequently, the thus-formed carboxylate anion reacts with the compound of the general formula $R^1$—Y.

When in the compound of the general formula $R^1$—Y Y represents a halide as an acid residue, i.e. the reactant is e.g. an alkyl halide, then the reaction can suitably be carried out in the presence of an organic aprotic polar solvent such as e.g. acetonitrile, dimethylformamide and the like in such a way that, when in the compound of the general formula (II) M stands for a metal atom or for an ammonium group, then the appropriate alkyl halide is added in a slight excess to the suspension containing the appropriate metal or ammonium salt, respectively, in a solvent. This reaction is performed at a temperature between 50° C. and 120° C. This method can preferably be used for preparing the compounds of the general formula (I) containing an R moiety which represents a —CO—$OR^1$ group where $R^1$ stands for an alkyl group containing 1 to 4 carbon atoms. A mixture of an organic solvent with water may also be employed as solvent but in this case the reaction is preferably carried out in the presence of a suitable phase transfer catalyst. E.g. a tetraalkylammonium halide may preferably be used for this purpose.

When in the compound of the general formula $R^1$—Y Y represents e.g. sulphate as an acid residue, the reactant may be e.g. an alkyl sulphate. The reaction of the compounds of general formula (II) with an alkyl sulphate represents a rarely used method of esterification or alkylation, respectively, in the chemistry of alkaloids and particularly in the field of vincamine derivatives. An especial benefit of this reaction consists in that the compounds desired are obtained selectively, in a high yield and without any quaternization. This process is particularly advantageous for preparing compounds of the general formula (I) containing an R moiety which represents a —CO—$OR^1$ group, wherein $R^1$ stands for an alkyl group containing 1 to 4 carbon atoms. This reaction can be accomplished in the presence of an inorganic base, e.g. an alkali metal hydroxide such as lithium, potassium or sodium hydroxide; or in the presence of an alkali carbonate, e.g. potassium or sodium carbonate; or by using ammonium hydroxide in the form of an aqueous solution. The alkyl sulphate reactant is used in a slight excess, suitably at room temperature. The use of water as solvent is preferable, though the reaction may be carried out in any inert organic solvent.

In process (a) of the invention, the starting materials of the formula (II) can be treated with any halogenating agent which is suitable to transform a carboxylic acid to an acyl halide. Appropriate halogenating agents may be e.g. thionyl halides such as thionyl chloride, thionyl bromide and the like. This halogenating reaction is suitably carried out by using an excess of the halogenating agent, e.g. of thionyl chloride, as solvent. Alternatively, this reaction may be accomplished in an inert aprotic organic solvent such as aromatic hydrocarbons, e.g. benzene, or in the presence of halogenated aliphatic hydrocarbons, e.g. chloroform. The temperature of this halogenation can be varied between wide limits, a suitable temperature interval is from 0° C. up to 100° C. After the halogenating reaction the compounds of the general formula (I), wherein R represents a —CO—X group (wherein X stands for a halogen atom), are obtained in the form of their hydrohalides. Subsequently, these hydrohalides are reacted, if desired, with a nucleophilic reagent of the general formula H—$OR^1$ or H—$NR^2R^3$. Such nucleophilic reactants may be e.g. optionally substituted aliphatic or aromatic alcohols, e.g. methanol or ethanol and the like; as well as benzyl alcohol, pyridylcarbinol, dimethylaminopropanol and the like; or ammonia, primary or secondary amines, e.g. diethylamine, benzylamine, piperidine, morpholine and the like. This reaction is carried out by using an inert organic solvent such as ether, halogenated aliphatic hydrocarbons, e.g. chloroform, or aromatic hydrocarbons, e.g. benzene or the like. Alternatively, this reaction can be realized in an excess of the nucleophilic reactant of the general formula H—$OR^1$ or H—$NR^2R^3$, respectively. The temperature of this reaction can be varied between wide limits; it is preferable, however, to accomplish this transformation at a temperature between 0° C. and 150° C. If desired, particularly when the nucleophilic compound is an alcohol of the general formula H—$OR^1$, an acid binding agent may also be used. Organic or inorganic bases, e.g. triethylamine, pyridine, anhydrous alkali metal carbonates, such as potassium or sodium carbonate and the like, can be used as acid binding agents. Of course, the nucleophilic reactant may also serve as an acid binding agent, particularly when this nucleophilic reactant is an aliphatic primary or secondary amine or an aromatic or an other cyclic amine of the general formula H—$NR^2R^3$. This process is particularly useful for preparing compounds of the general formula (I) containing an R moiety which represents a —CO—$OR^1$ group, wherein $R^1$ stands for an optionally mono- or polysubstituted aliphatic group containing 1 to 10 carbon atoms, an alicyclic group containing 3 to 8 carbon atoms or an aromatic hydrocarbyl group containing 6 to 14 carbon atoms. This process can be particularly useful when the reactivity or the tension of the nucleophilic reactant is relatively low or its use in excess is not advisable because of the difficult availability. Further on, this reaction can preferably be used for preparing compounds of the general formula (I) containing an R moiety which represents a —CO—NR$^2$R$^3$ group, wherein R$^2$ and R$^3$ are the same or different and each stands for a hydrogen atom or an alkyl group containing 1 to 4 carbon atoms and together they optionally form a saturated heterocycle with the adjacent nitrogen atom and optionally with one or more further nitrogen atoms or other neteroatoms. This reaction results in very high yields.

In process (a) of the invention, the compounds of the general formula (I), wherein R stands for a —CO—NR$^2$R$^3$ group, where both R$^2$ and R$^3$ are hydrogen atoms, may be dehydrated by e.g. a phosphorus oxyhalide compound. This reaction can suitably carried out in an excess of the dehydrating agent; alternatively, however, this transformation can be accomplished in the presence of an inert aprotic organic solvent such as aromatic hydrocarbons, e.g. benzene, or halogenated aliphatic hydrocarbons, e.g. chloroform. The dehydration is achieved by using preferably phosphorus oxychloride as phosphorus oxyhalide.

In process (b) of the invention, the compounds of the general formula (III) can directly be nitrated with fuming nitric acid in the presence of an inert organic solvent. On carrying out the nitration between 10° C. and 20° C., preferably at 16° C. in glacial acetic acid as solvent and adding ethanol to the reaction mixture, the appropriate 9-nitro-apovincaminic acid derivative is separated from the reaction mixture in crystalline form. However, when the nitration is directly realized at a lower temperature, between −10° C. and 0° C., and a halogenated hydrocarbon, e.g. chloroform, is used as solvent instead of the glacial acetic acid, then the appropriate 11-nitroapovincamic acid derivative is obtained by crystallizing the crude product from ethanol.

If desired, the alkyl esters of nitroapovincaminic acid of the general formula (I) containing 1 or 2 carbon atoms in the ester group may be subjected to transesterification. This transformation is suitably achieved in an excess of the alcohol component used for the esterification, possibly with the exclusion of water, by the simultaneous use of a catalyst, suitably a strong base in a preferably catalytic amount. Such bases are e.g. the alkali metal hydroxides, alkali metal alkoxides, preferably tertiary alkoxides such as potassium tertiary butoxide. The transesterification can be accomplished between wide temperature limits, suitably at a temperature from 50° C. to 150° C.

When desired, the alkyl esters of nitroapovincaminic acid of the general formula (I) containing 1 or 2 carbon atoms in the ester group may be amidated in a manner known in the art. This aminolysis can be achieved by heating an alkyl ester of nitroapovincaminic acid of the general formula (I) containing 1 or 2 carbon atoms in the ester group in an excess of the amine of the general formula H—NR$^2$R$^3$ used as solvent, preferably at the boiling temperature of the amine, then removing the excess amine by evaporation. This amide-forming reaction is particularly useful when the amine of the general formula H—NR$^2$R$^3$ used for the aminolysis is relatively non-volatile, i.e. when the boiling point of the amine is between 70° C. and 150° C. When the amine is relatively volatile, e.g. having a boiling point lower than 70° C., then the process (a) described above in detail can be used.

Within the amidating reaction, the formation of hydrazides, i.e. the preparation of the compounds of general formula (I) containing an R moiety which represents a —CO—NR$^2$R$^3$ group, wherein R$^2$ stands for a hydrogen atom and R$^3$ is an amino group, can be accomplished in a way similar to that described above. Thus, alkyl esters of nitroapovincaminic acid of the general formula (I) containing 1 or 2 carbon atoms in the ester group are reacted with a compound of the general formula H—NR$^2$R$^3$, wherein R$^2$ stands for a hydrogen atom and R$^3$ is an amino group, i.e. with a hydrazine derivative, e.g. with an excess of hydrazine hydrate.

When desired, the compounds of the general formula (I) prepared according to the process of the invention can be transformed to quaternary salts. For quaternization an alkyl halide such as a chloride, bromide, iodide or an alkyl sulphate is used in a slight excess over the equivalent amount. This reaction is suitably carried out in an inert anhydrous organic solvent such as aliphatic alcohols containing 1 to 6 carbon atoms, e.g. in the presence of absolute methanol, absolute ethanol and the like, or by using ketones, e.g. acetone or butanone, or a nitrile, e.g. acetonitrile, as solvent. The quaternization is accomplished suitably at higher temperatures.

When desired, the compounds of the general formula (I) prepared according to the process of the invention can be transformed to acid addition salts by using any one of the acids mentioned above.

The formation of the acid addition salts may be realized in any inert organic solvent such as an aliphatic alcohol containing 1 to 6 carbon atoms by dissolving a racemic or optically active compound of the general formula (I) in the above solvent and adding the appropriate acid or the solution of the appropriate acid in the above solvent to the solution of the compound of general formula (I) until the solution becomes slightly acidic (i.e. up to a pH value of about 5 to 6). Then, the acid addition salt precipitated from the mixture is separated in a suitable manner, e.g. by filtration.

Both the racemic and optically active compounds of the general formula (I) as well as the process for the preparation of these compounds are within the scope of the invention. On using a racemic starting material, a racemic final product is obtained; however, when an optically active starting material is employed, the final product is an optically active compound. A racemic final product can be resolved by using any of the known methods of resolution. However, the resolution can be realized in any step of the process of the invention.

When desired, the racemic and optically active compounds of the general formula (I) as well as their acid addition salts obtained by using the process of the invention can be subjected to further purification, e.g. to recrystallization. The utility of a solvent for recrystallization depends upon the solubility and crystallization characteristics of the solvent in question.

The racemic and optically active substances of the general formula (I) as well as their pharmaceutically acceptable acid addition and quaternary salts have valuable therapeutic properties, namely vasodilating, spasmolytic, antihypoxic and anticonvulsive effects.

The vasodilating effect was studied in dogs anaesthetized by a chloralose-pentobarbital mixture. The extremital blood flow was measured in the femoral artery, while the cerebral blood flow was observed in the internal carotid artery. Electromagnetic flow meters were used for measuring the blood flow. The substances under test were intravenously administered in a dose of 1 mg/kg of body-weight to 6 dogs and the percentage changes of the parameters measured were evaluated. Ethyl (+)-apovincamate, a commonly used therapeutic cerebral vasodilator was employed as reference drug.

| Circulatory effects (change in %) of 1 mg/kg of body-weight intravenous doses in anaesthetized dogs | | |
| --- | --- | --- |
| Compound | Carotid artery flow | Femoral flow |
| Ethyl (+)-apovincamate (reference drug) | +30 | +15 |
| Ethyl 9-nitroapovincamate | +95 | 0 |
| 2-Hydroxyethyl 9-nitroapovincamate | +45 | +10 |

The spasmolytic activity of the compounds was determined by using the traditional method, i.e. on the isolated guinea pig ileum [Magnus, R., Pflügers Arch. 102, 123 (1904)]. Papaverine and ethyl (+)-apovincamate used as therapeutic spasmolytics were used as reference drugs.

| Inhibition of barium-chloride-induced contraction of guinea pig ileum | |
| --- | --- |
| Compound | $ED_{50}$ µg/ml |
| Papaverine (reference drug) | 5.4 |
| Ethyl (+)-apovincamate (reference drug) | 2.0 |
| Ethyl 9-nitroapovincamate | 1.0 |
| Propyl 9-nitroapovincamate | 0.2 |
| Acetoxyethyl 9-nitroapovincamate | 0.4 |

According to one method, the antihypoxic activity was studied on conscious mice under normobaric hypoxia. Five male mice were placed in a glass cylinder of 3 liters volume flown through by a gas mixture containing 96% of nitrogen and 4% of oxygen. The time interval from the allocation up to the perishment of the animals was measured for 15 minutes as a maximum. The animals were considered as protected when they were alive for a twofold time length as compared to the time of perishment of the untreated animals. The compounds under test were intraperitoneally administered to 10 animals each in a dose of 50 mg/kg of body-weight 30 minutes before allocating in the glass cylinder.

| The antihypoxic effect of intraperitoneal doses of 50 mg/kg of body-weight on conscious mice under normobaric hypoxia | | |
| --- | --- | --- |
| | Time of survival | |
| Compound | Mean ± deviation min. | Protection % |
| Control | 6.0 ± 1.04 | — |
| Ethyl (+)-apovincamate (reference drug) | 6.4 ± 1.58 | 7 |
| Vincamine (reference drug) | 6.1 ± 1.30 | 2 |
| Ethyl 9-nitroapovincamate | 13.4 ± 2.37 | 123 / 80 |
| Acetoxyethyl 9-nitroapovincamate | 10.1 ± 3.51 | 68 / 30 |
| Ethyl 11-nitroapovincamate | 11.0 ± 3.35 | 83 / 50 |

The antihypoxic activity was investigated by using two other methods, too.

According to the asphyxic anoxia test [Caillard O. et al.: Life Sci. 16, 1607 (1975)], the animals were starved for 16 hours, then treated orally, and one hour following the treatment they were allocated in tightly closed glass bottles of 100 ml volume. The time of survival was registered as the time interval from closing the bottle up to the last respiration. The animals were considered as protected when they were alive for a time longer by 30% than the average time of survival of the control group.

According to the hypobaric hypoxia test [Baumel J. et al.: Proc. Soc. Bio. N.Y. 132, 629 (1969)], the animals were starved for 16 hours, then treated orally and one hour following the treatment they were allocated in an exsiccator where the pressure was decreased to 170 Hgmm within 20 seconds. The time of survival was registered from this time point up to the last respiration. The animals were considered as protected when they were alive for a time longer by 100% than the average time of survival of the control group. The $ED_{50}$ value (i.e. the dose which was effective in 50%) was calculated from the percentage of the protected animals by using the probit analysis method.

| Compound | Asphyxic anoxia | Hypobaric hypoxia |
| --- | --- | --- |
| | $ED_{50}$ mg/kg p.o. | |
| Mephenytoin (reference drug) | >80.0 | >80.0 |
| Ethyl (+)-apovincamate (reference drug) | >50.0 | >50.0 |
| 9-Nitro-apovincamic acid ethylester.HCl | 42.7 | >50.0 |

The anticonvulsive activity was studied by using the following methods.

On using the maximal electroshock model [Swinyard E. A. et at.: J. Pharmacol. Exp. Ther. 106, 319 (1959)], a shock (20 mA, 0.2 sec. HSE Shock Equipment Type 207) was given to mice weighing 22 to 24 g by using corneal electrodes. The animals were considered as protected the tonic extension of the lower extremities of which were abolished.

On using the metrazole seizure method [Everett, G. M. and Richards, R. K.: J. Pharmacol. Exp. Ther., 81, 402 (1944)], a subcutaneous dose of 125 mg/kg of pentylenetetrazole was administered to mice after pre-treatment. The persistant clonic convulsions as well as the tonic extensory convulsions abolished by the treatment were registered.

On using the strychnine seizure method [Kerley, T. L. et al.: J. Pharmacol. Exp. Ther., 132, 360 (1961)], tonic extensory convulsions were induced by an intraperitoneal dose of 2.5 mg/kg of strychnine nitrate. Such animals were considered as protected, the tonic extensory convulsions of which were abolished on effect of the treatment and the animals remained alive.

The neurotoxic side effects were observed by using the following methods.

On using the muscle incoordination model (rotarod method) [H. Kwibara et al.: Japan J. Pharmacol. 27, 117 (1977)], after a previous training the animals were selected which could reamin for 120 seconds on a horizontal rod of 20 mm in diameter rotating with 12 rpm. A muscle-incoordinating action was stated when the animals fell down from the rotating rod within the time limits.

On determining the muscle relaxant activity (traction test), male mice weighing 18 to 22 g were suspended by their upper legs on a horizontal wire of 5 mm in diameter. The animals wee considered as having hypomyotonia which did not draw up their lower legs to the upper ones on effect of the treatment within 5 seconds.

| Compound | Anticonvulsive effect | | | Neurotoxic effect | |
|---|---|---|---|---|---|
| | Max. electro-shock | Metrazole seizure | Strychnine seizure | Rotarod | Traction |
| | $ED_{50}$ mg/kg po. | | | $ED_{50}$ mg/kg po. | |
| Mephenytoin (reference drug) | 26.3 | 24.5 | 0 | 78.6 | 154.3 |
| 9-Nitro-apo-vincaminic acid ethylester.HCl | 25.6 | 27.6 | 20* | 180 mg/kg is ineffective | |

*by administering a dose of 30 mg/kg p.o. the inhibition is 20° C.

On the basis of the above investigations it can be stated that the biological activity is very preferably influenced by a substitution with a nitro group in the ring "A". This is shown by the fact that the cerebral vasodilating effect is significantly increased as compared to a reference drug having a similar chemical structure. Further on, this vasodilating action appears specifically in the brain regions and is not or only hardly observed in the blood vessels of the extremities which is different from the mode of action of the reference drug.

In addition to the circulatory effects, the compounds of the invention possess a significant protecting activity against a cerebral hypoxic damage causing the death of the animals. This effect may be accompanied by an increase in the circulation but it may also appear as an independent action on the brain metabolism, which means that the brain cells are capable to continue their function in spite of the low oxygen supply. The compounds of the invention considerably increase the tolerancy of the animals in heavy hypoxic states dangerous to life.

The compounds exert spasmolytic effect, too, which has been shown on unstriped intestine muscle. This effect is essentially higher than that of papaverine used as reference substance. The compounds having an essential spasmolytic property generally show an expressed circulatory effect and also bear an antihypoxic activity emphasizing a preferably pharmacological action exerted on the cells or on the cell membranes which is particularly important under pathological conditions.

The quality and strength of the anticonvulsive action of the compounds of the invention are similar to those of mephenytoin used as reference drug; however, no neurotoxic side effect is observed after administration of the 6-fold of the anticonvulsive dose. Thus, the therapeutic index (i.e. the ratio of the neurotoxic $ED_{50}$ to the anticonvulsive $ED_{50}$) is more advantageous than that of the reference drug.

The active compounds of the general formula (I) can be transformed to pharmaceutical compositions by mixing them with the usual non-toxic inert solid or liquid carriers and/or additive materials which are commonly used in these compositions and are useful for parenteral or enteral administration. As carriers e.g. water, gelatine, lactose, starch, pectin, magnesium stearate, stearic acid, talc and vegetable oils such as peanut oil, olive oil or the like can be employed. The active ingredients can be formulated to the usual pharmaceutical compositions e.g. to solid forms (such as rounded or angled tablets, dragées, capsules, e.g. hard gelatine capsules, pills, suppositories or the like) or to liquid forms (such as oily or aqueous solutions, suspensions, emulsions, syrups, soft gelatine capsules, injectable oily or aqueous solutions or suspensions and the like). The amount of the solid carrier materials can be varied between wide limits, preferably they are used in an amount between about 25 mg and 1 g. The compositions may optionally contain commonly used pharmaceutical additives, e.g. preserving agents, stabilizers, wetting (surface active9 and emulsifying agents, as well as salts useful for adjusting the osmotic pressure, buffers, aromatizing and flavouring agents and the like. Further on, the compositions may optionally contain other known, therapeutically valuable compounds. The composition is preferably formulated in a unit dosage form useful for the desired route of administration.

The pharmaceutical compositions are prepared by using the common methods involving e.g. sieving, mixing, granulating and pressing or dissolving the components for transforming them to the appropriate compositions. The compositions may be subjected to further operations (e.g. sterilization) commonly used in the pharmaceutical industry.

The invention is illustrated in detail by the aid of the following non-limiting Examples.

Example 1

Preparation of 9-nitroapovincamine

A mixture containing 3.6 g (0.01 mole) of (+)-9-nitroapovincaminic acid, 50 ml of acetone, 10 ml of 1N aqueous sodium hydroxide solution and 1 ml (0.011 mole) of methyl sulphate is stirred at room temperature for 2 hours. Then the pH value of the mixture is adjusted to a value between 7 and 8 by adding concentrated aqueous ammonium hydroxide solution and the solution obtained in concentrated to the two-thirds of its original volume under reduced pressure. The crystals precipitated are filtered, washed thoroughly with water and dried to give 3.4 g (90% yield) of the aimed compound, m.p.: 160°–161° C., $[\alpha]_D = +12.5°$ (c=0.4, pyridine).

The spectral data of the compound are in accordance with the literature.

Example 2

Preparation of 9-nitroapovincamine monohydrochloride

The solution of 3.6 g (0.01 mole) of (+)-9-nitroapovincamaninic acid in 200 ml of anhydrous methanol is saturated with dry gaseous hydrogen chloride under cooling in the presence of 2 g of a molecular sieve (3 Å, Aldrich 20,859-2). Then the reaction mixture is refluxed while introducing gaseous hydrogen chloride for 2 hours. The molecular sieve is removed by filtering and washed with methanol. The solution is combined with the washings and evaporated to give 4.1 g (99% yield) of the crude hydrochloride. This crude product is dissolved in 20 ml of acetone and precipitated by adding 20 ml of ether. The crystals are filtered, washed with an 1:1 mixture of ether and acetone and dried to give 3.4 g (82% yield) of the aimed compound, m.p.: 185°–188° C.

Example 3

Preparation of 11-nitroapovincamine

The process described in Example 1 is followedd except that 3.6 g (0.01 mole) of (+)-11-nitroapovincaminic acid are used as starting material to give 3.2 g (85% yield) of the aimed compound, m.p.: 137°–139° C.; $[\alpha]_D = +31.25°$ (c=0.4; pyridine).

The spectral data of the compound are in accordance with the literature.

Example 4

Preparation of 11-nitroapovincamine

The process described in Example 1 is followed except that 3.6 (0.01 mole) of (+)-11-nitroapovincaminic acid are used as starting material to give 3.9 g (95% yield) of 11-nitroapovincamine monohydrochloride which are dissolved in a mixture of 50 ml of water and 50 ml of ethyl acetate and alkalized by using concentrated aqueous ammonium hydroxide solution. The ethyl acetate layer is separated, the aqueous phase is twice extracted with 30 ml of ethyl acetate each, then the organic phases are combined and washed three times with 20 ml of water each. The organic phase is dried over anhydrous sodium sulphate, filtered and the filtrate is evaporated. The evaporation residue is thoroughly mixed with ether to give 3.2 g (85% yield) of the aimed compound, m.p.: 137°–139° C.

Example 5

Preparation of ethyl 9-nitroapovincamate monohydrochloride

The solution of 3.6 g (0.01 mole) of (+)-9-nitroapovincaminic acid in 200 ml of anhydrous methanol is saturated with dry gaseous hydrogen chloride in the presence of 2 g of a molecular sieve (3 Å, Aldrich 20,859-2) under cooling. Then the reaction mixture is refluxed while introducing gaseous hydrogen chloride for 2 hours. The molecular sieve is removed by filtering and washed with ethanol. The ethanolic solution is evaporated to give 4.3 g (99% yield) of the crude hydrochloride as evaporation residue which is rubbed with 10 ml of acetone. The crystals obtained are filtered, washed with 5 ml of acetone and dried to give 3.7 g (88% yield) of the aimed compound, m.p.: 220°–224° C.

Analysis: Calculated for $C_{22}H_{26}N_3O_4Cl$ (molecular weight 431.99): C 61.16; H 6.06; N 9.72; Cl 8.22%; Found: C 61.14; H 6.60; N 9.57; Cl 8.11%.

Example 6

Preparation of ethyl 9-nitroapovincamate

A solution containing 9.0 g (0.023 mole) of (+)-9-nitroapovincamine and 0.3 g of potassium tertiarybutoxide in 250 ml of anhydrous ethanol is refluxed for 2 hours, then evaporated to dryness. The residue is taken up in a mixature of 350 ml of dichloromethane and 100 ml of water. After separating the layers, the dichloromethane solution is washed twice with 100 ml of water each, the organic phase is dried over anhydrous sodium sulphate, filtered and evaporated. The oily residue is rubbed with 50 ml of ether to give yellow crystals which are filtered, washed with ether and dried to give 8.3 g (91% yield) of the aimed compound, m.p.: 125°–126° C., $[\alpha]_D = +241.9°$ (c=1, chloroform).

$^1$H—NMR spectrum (CDCl$_3$, δ ppm): ET=1.02 (t) 3, 1.93 (q) 2; EtO=1.39 (t) 3, 4.40 (q) 2; H-3=4.11 (s) 1; H-15=6.28 (s) 1; H-10=7.85 (dd) 1 (J=8 and 1 Hz); H-11=7.10 (t) 1 (J=8 Hz); H-12=7.41 (dd) 1 (J=8 and 1 Hz); skelton protons==1.3–3.4 (m) 10.

Example 7

Preparation of ethyl 11-nitroapovincamate

A mixture containing 7.3 g (0.02 mole) of (+)-11-nitroapovincaminic acid, 100 ml of acetone, 20 ml of 1N aqueous sodium hydroxide solution and 3 ml (0.023 mole) of ethyl sulphate is stirred at room temperature for 3 hours. Then the pH value of the mixture is adjusted to 8 by adding concentrated aqueous ammonium hydroxide solution and the mixture is concentrated under reduced pressure. The precipitated crystals are filtered, washed with water and dried to give 6.8 g (86% yield) of the aimed compound, m.p.: 166°–167° C., $[\alpha]_D = +110.98°$ (c=0.4, chloroform).

$^1$H—NMR spectrum (CDCl$_3$, δ ppm): Et=1.02 t (3), 1.93 q (2) EtO=1.41 t (3), 4.46 q (2); H-3=4.11 s (1); H-15=6.30 s (1); H-9=7.41 d (1) (J=8.8 Hz); H-10=7.96 dd (1) (J=8.8 and 2 Hz); H-12=8.2 d (1) (J=2 Hz), skeleton protons: 1.66–3.5 m (10).

Example 8

Preparation of ethyl 11-nitroapovincamate monohydrochloride

A solution containing 4 g (0.011 mole) of ethyl (+)-apovincamate in 20 ml of chloroform is cooled to −5° C., 4 ml of fuming nitric acid (d=1.52) dissolved in 16 ml of glacial acetic acid are dropwise added to the solution at the same temperature, then the mixture is stirred at a temperature between −5° C. and −2° C. for 30 minutes. The reaction mixture is poured onto 200 g of broken ice and 20 ml of chloroform are added. The mixture is alkalized to pH 8 by adding concentrated aqueous ammonium hydroxide solution while stirring. The organic layer is separated the aqueous phase is extracted twice with 10 ml of chloroform each and the organic phases are combined, washed with 20 ml of water, dried over anhydrous sodium sulphate, filtered and evaporated. The residue (4.3 g) is dissolved in 20 ml of hot ethanol and set aside in the refrigerator for 2 days. The precipitated crystals are filtered and washed with 5 ml of cold ethanol to give 1.3 g (30% yield) of ethyl 11-nitroapovincamate, m.p.: 182°–186° C. This product is transformed to the aimed hydrochloride compound in acetone solution by adding an ethanolic hydrogen chloride solution.

Analysis: Calculated for $C_{22}H_{26}N_3O_4Cl$ (molecular weight 431.99): C 61.16; H 6.06; N 9.72; Cl 8.22%; Found C 60.98; H 6.24; N 9.74; Cl 8.13%.

Example 9

Preparation of ethyl 11-nitroapovincamate 7.3 g (0.02 mole) of (+)-11-nitroapovincaminic acid and 0.12 g of potassium hydroxide are dissolved in 20 ml of anhydrous ethanol. The ethanol is distilled off from this solution, the remained yellow crystalline potassium salt is suspended in 25 ml of acetonitrile, then 0.18 ml of ethyl iodide is added to this suspension. The mixture is refluxed while stirring for 3 hours, then the solvent is evaporated under reduced pressure. The residue is taken up in 50 ml of water and 50 ml of ethyl acetate, the mixture is alkalized to pH 8, and after shaking thoroughly the phases are separated. The aqueous layer is washed twice with 20 ml of ethyl acetate each, the combined organic solution is washed three times with 10 ml of water each, dried over anhydrous sodium sulphate, filtered and evaporated to dryness. The residue is rubbed with 10 ml of ether, the yellow crystals obtained are filtered and washed with ether to give 6.8 g (86% yield) of the aimed compound, m.p.: 166°–167° C., $[\alpha]_D = 110.98°$ (c=0.4, chloroform).

Example 10

Preparation of 11-nitroapovincaminic acid chloride monohydrochloride

A mixture of 3.67 g (0.01 mole) of (+)-11-nitroapovincaminic acid with 10 ml of thionyl chloride is refluxed for 90 minutes, then evaporated to dryness under reduced pressure. 10 ml of benzene are added to the residue and the evaporation is repeated. The residue is rubbed with 10 ml of ether, the crystals obtained are filtered and washed with ether to give 4.1 g (97% yield) of the aimed compound; m.p.: 224°–227° C.

Example 11

Preparation of 3-dimethylaminopropyl 11-nitroapovincamate dihydrochloride 1.6 g (0.0038 mole) of the acid chloride prepared in Example 10 are stirred with 1.3 ml (0.011 mole) of 3-dimethylaminopropanol in 10 ml of chloroform at room temperature. After 30 minutes, 10 ml of chloroform and 5 ml of water are added to the mixture. The phases are separated, the organic phase is washed three times with 5 ml of water each, dried over anhydrous sodium sulphate, filtered and the chloroform is evaporated from the filtrate to give 1.6 g (93.5% yield) of the oily base form of the aimed compound.

$^1$H—NMR (CDCl$_3$, δ): Et: 1.03 t (3), 1.93 q (2); N(CH$_3$)$_2$: 2.22 s (6), H-3: 4.13 s (1); OCH$_2$: 4.46 t (2); H-15: 6.32 s (1); H-9: 7.32 d (1) (J=9 Hz); H-10: 7.97 dd (1) (J=9 and 2 Hz); H-12: 8.22 d (1) (J=2 Hz); skeleton protons +N—CH$_2$CH$_2$: 1.10–3.44 m (14).

This base (1.6 g) is dissolved in 20 ml of acetone, the pH value of the obtained solution is adjusted to 4 by adding ethanolic hydrogen chloride solution, the precipitated crystals are filtered and washed with acetone to give 1.27 g (64% yield) of the aimed compound, m.p.: 171°–176° C. (with decomposition).

Analysis: Calculated for C$_{25}$H$_{32}$N$_4$O$_4$.2HCl (molecular weight 525.35): C 57.15; H 6.47; N 10.65; Cl 13.49%; Found C 57.10; H 6.60; N 10.62; Cl 13.56%.

Example 12

Preparation of benzyl 11-nitroapovincamate and its monohydrochloride

According to Example 10, 1.6 g (0.0038 mole) of 11-nitroapovincaminic acid chloride hydrochloride are prepared from the acid, dissolved in 10 ml of benzyl alcohol and stirred at 100° C. for 3 hours. After cooling, 10 ml of water are added and the solution obtained is adjusted to pH 8 by adding concentrated aqueous ammonium hydroxide solution. The mixture is extracted three times with 20 ml of ethyl acetate each. The combined organic solution is washed twice with 10 ml each of saturated aqueous sodium chloride solution and 10 ml of water and the solvent is evaporated under reduced pressure to give 1.66 g (95.9% yield) of the base form of the aimed compound as an evaporation residue.

$^1$H—NMR (CDCl$_3$, δ): Et: 1.00 t (3), 0.91 q (2); H-3: 4.10 s (1); OCH$_2$: 5.34 d (1) and 5.50 d (1) (J$_{gem}$=12 Hz); H-15: 6.35 s (1); H-10: 7.95 dd (1) (J=9 Hz and 2 Hz); H-12: 8.22 d (1) (J=2 Hz); other Ar—H: 7.20–7.50 m (6); skeleton protons: 1.10–3.40 m (10).

The above base is dissolved in 100 ml of ether and this solution is acidified to pH 4 by adding an ethanolic hydrogen chloride solution. The precipitated crystals are filtered, washed with ether and recrystallized from 20 ml of ethanol to give 0.99 g (53% yield) of the monohydrochloride form of the aimed compound, mp.: 146°–150° C.

Analysis: Calculated for C$_{27}$H$_{27}$N$_3$O$_4$.HCl (molecular weight 493.92): C 65.65; H 5.66; N 8.50; Cl 7.17%; Found C 65.48; H 5.82; N 8.54; Cl 7.26%.

Example 13

Preparation of 3-pyridylmethyl 11-nitroapovincamate

According to Example 10, 1.6 g (0.0038 mole) of 11-nitroapovincaminic acid chloride hydrochloride are prepared from the acid, dissolved in 20 ml of chloroform and stirred with 1.5 ml (0.015 mole) of 3-pyridylmethanol at room temperature for 3 hours. Then 10 ml of water are added and the solution is alkalized to pH 8 by adding saturated aqueous sodium carbonate solution. The phases are separated and the organic solution is washed three times with 10 ml of water each, dried over anhydrous sodium sulphate and evaporated to dryness under reduced pressure. The oily residue is dissolved in 10 ml of hot methanol and clarified. After cooling the crystalline substance is filtered, washed with cold methanol and dried to give 1.42 g (82% yield) of the aimed compound, m.p.: 136°–138° C.

$^1$H—NMR (CDCl$_3$, δ): Et: 1.10 t (3); 1.92 q (2); H-3: 4.15 s (1); CH$_2$—O: 5.38 d (1) and 5.48 d (1) (J$_{gem}$=12 Hz); H-15: 6.36 s (1); H-9: 7.44 d (1) (J=9 Hz); H-10: 7.98 dd (1) (J=9 and 2 Hz); H-12: 8.16 d (1) (J=2 Hz); Ar—H (pyridine): 8.68 dd (1); 8.58 dd (1), 7.82 t (1), 7.33 ddd (1); skeleton protons: 1.20–3.40 m (10).

Analysis: Calculated for C$_{26}$H$_{26}$N$_4$O$_4$ (molecular weight 458.46): C 68.11; H 5.67; N 12.21%; Found C 68.25; H 5.58; N 12.08%.

Example 14

Preparation of 2-hydroxyethyl 11-nitroapovincamate

A solution containing 1.85 g (0.0049 mole) of (+)-11-nitroapovincamine and 0.1 g of potassium tertiary-butoxide in 60 ml of ethylene glycol is stirred at 120° C. for 90 minutes. After cooling, 30 ml of water are added to the solution, the precipitated crystalline substance is filtered, washed four times with 25 ml of water each and dried to give 1.9 g (95% yield) of the aimed compound, m.p.: 227°–229° C.

Example 15

Preparation of 2-hydroxyethyl 9-nitroapovincamate

A solution containing 1.85 g (0.0049 mole) of (+)-9-nitroapovincamine and 0.1 g of potassium tertiary-butoxide in 60 ml of ethylene glycol is stirred at 120° C. for 90 minutes. Then the mixture is evaporated to the three-quarters of its original volume under reduced pressure, the residue is dissolved in 50 ml of ethyl acetate and this solution is washed three times with 20 ml of water each. The ethyl acetate layer is dried over anhydrous sodium sulphate, filtered and evaporated. The residue is rubbed with ether, the crystals obtained are filtered and washed with ether to give 1.47 g (74% yield) of the aimed compound, m.p.: 152°–154° C.

$^1$H—NMR (CDCl$_3$, δ ppm): Et: 1.00 t (3), 1.90 q (2); H-3: 3.92 s (1); CH$_2$OCO—: 4.45 m (2); HO—CH$_2$—: 3.90 m (2); H-15: 6.32 s (1); Ar—H: 7.18–8.00 m (3).

Example 16

Preparation of 2-methylpropyl 9-nitroapovincamate and its monohydrochloride

A solution containing 1 g (0.0026 mole) of (+)-9-nitroapovincamine and 0.01 g of potassium tertiary-butoxide in 30 ml of anhydrous isobutanol is refluxed for 30 minutes, then evaporated to dryness under reduced pressure. The residue is dissolved in 50 ml of ethyl acetate and washed three times with 20 ml of water each. The ethyl acetate layer is dried, filtered and evaporated to give 1.09 g (99% yield) of the base form of the aimed compound as a residue.

$^1$H—NMR (CDCl$_3$, δ): Ar—H: 7.06-8.1 m (3); H-15: 6.34 s (1); H-3: 4.12 s (1); —CH$_2$—O: 4.20 d (2).

The above base is dissolved in 10 ml of acetone and this solution is acidified to pH 4 by adding an ethanolic hydrogen chloride solution. The precipitated yellow crystals are filtered, washed with cold acetone and dried to give 0.73 g (62% yield) of the monohydrochloride form of the aimed compound, m.p.: 222°-224° C.

Analysis: Calculated for C$_{24}$H$_{29}$N$_3$O$_4$.HCl (molecular weight 459.89): C 62.67; H 6.30; N 9.13; Cl 7.70%; Found C 62.76; H 6.80; N 9.10; Cl 7.87%.

Example 17

Preparation of octyl 9-nitroapovincamate monohydrochloride

A solution containing 1 g (0.0026 mole) of (+)-9-nitroapovincamine in 10 ml of capryl alcohol is heated with 0.01 g of potassium tertiary-butoxide at 140° C. for 20 hours. The mixture is evaporated to dryness under reduced pressure, the residue is dissolved in 50 ml of ethyl acetate and extracted three times with 20 ml each of 1N hydrochloric acid solution. The ethyl acetate solution is evaporated to dryness, the residue is dissolved in 10 ml of acetone and this solution is acidified to pH 3 by adding an ethanolic solution of hydrogen chloride. After the addition of 10 ml of diisopropyl ether, the mixture is cooled in the refrigerator overnight, then the precipitated crystals are filtered, washed with ether and dried to give 0.71 g (53% yield) of the aimed compound, m.p.: 168°-172° C.

Analysis: Calculated for C$_{28}$H$_{37}$N$_3$O$_4$.HCl (molecular weight 516.04): C 65.11; H 7.36; N 8.13; Cl 6.86%; Found C 65.45; H 7.82; N 8.12; Cl 6.90%.

Example 18

Preparation of propyl 9-nitroapovincamate monohydrochloride

A solution containing 1.5 g (0.004 mole) of (+)-9-nitroapovincamine and 0.1 g of potassium tertiary-butoxide in 150 ml of anhydrous propanol is refluxed for 10 hours, then the solution is evaporated to dryness, the residue is dissolved in 60 ml of ethyl acetate and extracted three times with 20 ml of water each. The ethyl acetate solution is dried over anhydrous sodium sulphate and evaporated to dryness under reduced pressure. The residue (1.5 g, i.e. 92%) is dissolved in the mixture of 2 ml of acetone and 20 ml of ether and the solution is acidified to pH 3 by adding an ethanolic hydrogen chloride solution. The precipitated crystals are filtered, washed with ether and dried to give 1.34 g (76% yield) of the aimed compound, m.p.: 199°-204° C.

Analysis: Calculated for: C$_{23}$H$_{27}$N$_3$O$_4$.HCl (molecular weight 446.92): C 61.89; H 6.27; N 9.41; Cl 7.95%; found C 62.00; H 6.46; N 9.40; Cl 7.88%.

Example 19

Preparation of 9-nitroapovincaminic acid amide and its monohydrochloride

5 ml of thionyl chloride are added to 1.84 g (0.005 mole) of (+)-9-nitroapovincaminic acid, then the mixture is refluxed under stirring. After boiling one hour, the solution obtained is evaporated to dryness and 20 ml of benzene are added to the residue. The precipitated crystals are filtered, washed three times with 10 ml of benzene each and dried to give 1.6 g (74% yield) of 9-nitroapovincaminic acid chloride hydrochloride, m.p.: 238°-240° C. This substance is added in little portions to 100 ml of ether saturated with gaseous ammonia while stirring and cooling with ice. The mixture is stirred further at 0° C. for 2 hours and for additional 2 hours at room temperature. The pH value of the mixture is maintained between 8 and 9 by adding an ethereal ammonia solution when needed. The crystals obtained are filtered, washed with ether and then three times with 20 ml of water each to give 1.37 g (75% yield) of the base form of the aimed compound, m.p.: 270°-274° C.

This base is suspended in 5 ml of ethanol and acidified to pH 3 by adding an ethanolic hydrogen chloride solution. After adding 2 ml of ether the precipitated crystals are filtered, washed with ether and dried to give 1.62 g (81% yield) of the aimed compound, m.p.: 256°-260° C.

Analysis: Calculated for C$_{20}$H$_{22}$N$_4$O$_3$.HCl (molecular weight 402.87): C 59.62; H 5.75; N 13.9; Cl 8.79%; Found C 59.32; H 6.00; N 14.00; Cl 8.65%.

Example 20

Preparation of 9-nitroapovincaminic acid nitrile and its monohydrochloride

A mixture containing 3.66 g (0.01 mole) of 9-nitroapovincaminic acid amide and 10 ml of phosphorus oxychloride is refluxed and then evaporated to dryness under reduced pressure. The residue is dissolved in 100 ml of dichloroethane and this solution is alkalized to pH 8 by adding 1N aqueous sodium hydroxide solution. The aqueous layer is separated, the dichloroethane phase is washed three times with 30 ml of water each, dried over anhydrous sodium sulphate, filtered and evaporated to dryness. The residue is dissolved in 15 ml of hot methanol and cooled. The precipitated crystals are filtered, washed with cold methanol and dried to give 2.7 g (77% yield) of the base form of the aimed compound, m.p.: 139°-142° C.

$^1$H—NMR (CDCl$_3$, δ): Et: 1.04 t (3), 1.91 q (2); H-3: 4.24 s (1); H-15: 6.15 s (1); H-10: 7.95 dd (1); H-11: 7.29 t (1); H-12: 8.35 dd (1); skeleton protons: 0.90-3.40 m (10).

A solution containing 0.35 g (0.001 mole) of the above base in 5 ml of acetone is acidified to pH 3 by adding an ethanolic hydrogen chloride solution. After addition of 2 ml of ether the precipitated crystals are filtered, washed with ether and dried to give 0.28 g (73% yield) of the monohydrochloride form of the aimed compound, m.p.: 219°-222° C.

Analysis: Calculated for C$_{20}$H$_{20}$N$_4$O$_2$.HCl (molecular weight 383.86): C 62.42; H 5.24; N 14.56; Cl 9.21%; Found C 62.56; H 5.87; N 14.63; Cl 9.80%.

Example 21

Preparation of 11-nitroapovincaminic acid diethylamide

A solution containing 0.42 g (0.001 mole) of 11-nitroapovincaminic acid chloride hydrochloride and 2 ml of diethylamine in 10 ml of dichloroethane is stirred for one hour, then the mixture is extracted three times with 20 ml of water each, the organic phase is dried over anhydrous sodium sulphate, filtered and evaporated to dryness. The residue is recrystallized from a mixture of 3 ml of methanol and 5 ml of ether, to give 0.29 g (69% yield) of the aimed compound, m.p.: 140°–141° C.

Analysis: Calculated for $C_{24}H_{30}N_4O_3$ (molecular weight 422.51): C 68.22; H 7.16; N 13.26%; Found C 68.40; H 7.88; N 13.30%.

Example 22

Preparation of 9-nitroapovincaminic acid 4-methylpiperidide and its monohydrochloride A solution of 2.4 ml (0.04 mole) of 4-methylpiperidine in 10 ml of benzene is added portionwise to a suspension containing 2.11 g (0.005 mole) of 9-nitroapovincaminic acid chloride hydrochloride in 25 ml of anhydrous benzene at room temperature while stirring, then the mixture is refluxed for one hour and evaporated to dryness under reduced pressure. The residue is taken up in 50 ml of ethyl acetate and 50 ml of water, the phases are separated and the organic layer is washed twice with 30 ml of water each. After drying over anhydrous sodium sulphate the organic solution is filtered and evaporated to dryness. The residue is mixed with 20 ml of ether and the preciptated crystals are filtered and washed with ether to give 1.86 g (83% yield) of the base form of the aimed compound, m.p.: 198°–200° C.

This base is dissolved in 50 ml of ether while stirr acidified to pH 3 by adding an ethanolic hydrogen chloride solution and stirred for additional 2 hours at room temperature. The precipitate is filtered, washed with ether and dried to give 1.69 g (70% yield) of the monohydrochloride form of the aimed compound, m.p.: 216°–220° C.

Analysis: Calculated for $C_{26}H_{32}N_4O_3 \cdot HCl$ (molecular weight 485.02): C 64.38; H 6.85; N 11.55; Cl 7.31%; Found C 64.47; H 7.01; N 11.65; Cl 7.28%.

Example 23

Preparation of phenyl 11-nitroapovincamate

A mixture of 1.0 g (0.0027 mole) of 11-nitroapovincaminic acid with 10 ml of thionyl chloride is refluxed for one hour, then the excess of thionyl chloride is removed under reduced pressure. The residue is mixed with 20 ml of anhydrous benzene and the distillation is repeated under reduced pressure. This operation is repeated. The residue obtained is dissolved in 10 ml of anhydrous acetone and dropwise added to a mixture containing 0.28 g (0.003 mole) of phenol, 10 ml of acetone and 6 ml of 1N aqueous sodium hydroxide solution at 0° C. while stirring. The mixture is stirred for 2 hours, then evaporated to dryness under reduced pressure. The residue is dissolved in 50 ml of ethyl acetate and extracted three times with 20 ml of water each. The organic phase is dried over anhydrous sodium sulphate, filtered and evaporated to dryness. After adding 20 ml of petroleum ether to the residue, the precipitated crystals are filtered, washed with petroleum ether and dried to give 0.63 g (52% yield) of the aimed compound, m.p.: 96°–98° C.

Example 24

Preparation of 11-nitroapovincaminic acid hydrazide

A mixture containing 0.48 g (0.0013 mole) of 11-nitroapovincaminic acid and 5 ml of thionyl chloride is refluxed for one hour, then the excess of thionyl chloride is removed under reduced pressure. The residue is mixed with 10 ml of anhydrous benzene and evaporated to dryness under reduced pressure. This operation is repeated. The residue obtained is dissolved in 5 ml of anhydrous acetone and dropwise added to the solution of 7 ml of hydrazine hydrate in 10 ml of acetone at 0° C. while stirring. The mixture is stirred at the same temperature for one hour, then evaporated to dryness under reduced pressure. The residue is dissolved in 50 ml of ethyl acetate and extracted three times with 30 ml of water each. The organic phase is dried over sodium sulphate, filtered and evaporated to dryness. After rubbing the residue with hexane, the precipitated crystals are filtered, washed with hexane and dried to give 0.34 g (68% yield) of the aimed compound, m.p.: 143°146° C.

Example 25

Preparation of propargyl 9-nitroapovincamate monohydrochloride 2.0 g (0.0048 mole) of the acid chloride prepared in Example 10 are added to a solution containing 0.23 g of sodium in 5 ml of propargyl alcohol at room temperature under stirring. The mixture is stirred at room temperature for one hour, then evaporated. The residue is taken up in 50 ml of ethyl acetate and washed three times with 20 ml of water each. The organic phase is dried over anhydrous sodium sulphate and evaporated to give 1.6 g (82% yield) of the base form of the aimed compound as an oily residue.

This base is dissolved in 10 ml of acetone and after adding 10 ml of ether the mixture ia acidified to pH 4 by adding an ethanolic solution of hydrogen chloride. The precipitated crystals are filtered, washed with a 1:1 mixture of ether and acetone and dried to give 1.6 g (75% yield) of the monohydrochloride form of the aimed compound, m.p.: 205°–108° C.

Example 26

Preparation of 2'-trifluoroethyl 9-nitroapovincamate monohydrochloride

A mixture containing 2 g (0.0048 mole) of the acid chloride prepared in Example 10 in 10 ml of trifluoroethanol is stirred with 2 ml of triethylamine at room temperature for one hour. The mixture is evaporated, the residue is taken up in 50 ml of ethyl acetate and washed three times with 20 ml of water each. The organic phase is dried over anhydrous sodium sulphate and evaporated to give 1.55 g (72% yield) of the base form of the aimed compound as evaporation residue.

This base is dissolved in the mixture of 10 ml of acetone with 50 ml of ether and acidified to pH 4 by adding ethanolic hydrogen chloride solution. The crystalline precipitate is filtered and washed with ether to give 1.58 g (68% yield) of the monohydrochloride form of the aimed compound, m.p.: 200°–205° C.

Example 27

Preparation of allyl (+)-9-nitroapovincamate monohydrochloride

A mixture containing 2 g (0.0052 mole) of (+)-9-nitroapovincamine and 0.01 g of potassium tertiary-butoxide in 25 ml of anhydrous allyl alcohol is refluxed for 8 hours, then the mixture is evaporated to dryness under reduced pressure. The residue is dissolved in 50 ml of ethyl acetate and washed three times with 20 ml of water each. After drying the organic layer over anhydrous sodium sulphate, the solution is evaporated to dryness under reduced pressure to give 1.9 g (90% yield) of the base form of the aimed compound as an oily evaporation residue.

This oily base is dissolved in 50 ml of ether and acidified to pH 4 by adding an ethanolic hydrogen chloride solution. The precipitated yellow crystalline substance is filtered, washed with ether and dried to give 1.6 g (69% yield) of the monohydrochloride form of the aimed compound, m.p.: 193°–197° C., $[\alpha]_D^{20} = +264.97°$ (c=0.2, ethanol).

Example 28

Preparation of propyl (+)-9-nitroapovincamate 4-methoidide 1.2 ml of methyl iodide are added to a solution containing 1.5 g of propyl (+)-9-nitroapovincamate in 10 ml of acetone. The mixture is stirred at room temperature for 2 hours, then set aside in the refrigerator overnight. The precipitated yellow crystals are filtered, washed with acetone and dried to give 1.32 g (68% yield) of the aimed compound, m.p.: 190°–192° C., $[\alpha]_D^{20} = +116.64°$ (c=2.0, chloroform).

Example 29

Preparation of cyclopentyl 9-nitroapovincamate monohydrochloride 0.23 g of sodium is added to the mixture of 15 ml of anhydrous benzene and 5 ml of cyclopentanol and the mixture is refluxed until the sodium metal is dissolved. After cooling to room temperature, 2.0 g (0.0048 mole) of 9-nitroapovincaminic acid chloride hydrochloride prepared in Example 10 are added portionwise to the solution under stirring and the mixture is refluxed for one hour. After cooling 50 ml of ethyl acetate are added, washed three times with 20 ml of water each, and after drying the organic phase over anhydrous sodium sulphate the solution is evaporated to dryness under reduced pressure to give 1.3 g of the base form of the aimed compound as an evaporation residue. This base is dissolved in 50 ml of ether and acidified to pH 4 by adding an ethanolic hydrogen chloride solution. The precipitated yellow crystals are filtered, washed with ether and dried to give 1.06 g (49% yield) of the monohydrochloride form of the aimed compound, m.p.: 210°–215° C. (with decomposition).

In addition to the compounds named above, specific reference is made to the following compounds:
dimethylaminopropyl 9-nitroapovincamate,
benzyl 9-nitroapovincamate,
3-pyridylmethyl 9-nitroapovincamate,
isobutyl 11-nitroapovincamate,
octyl 11-nitroapovincamate,
propyl 11-nitroapovincamate,
11-nitroapovincaminic acid amide,
11-nitroapovincaminic acid nitrile,
9-nitroapovincaminic acid diethylamide,
11-nitroapovincaminic acid 4-methylpiperidide,
phenyl 9-nitroapovincamate,
9-nitroapovincaminic acid hydrazide,
propargyl 11-nitroapovincaminate,
2'-trifluoroethyl 11-nitroapovincaminate,
allyl 11-nitroapovincaminate,
cyclopentyl 11-nitroapovincaminate.

We claim:

1. Racemic and optically active 9- and 11-nitroapovincaminic acid derivatives of the formula I

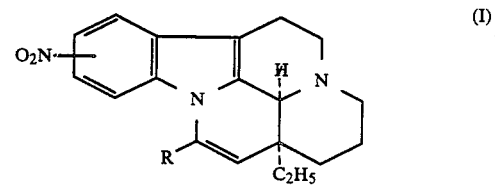

wherein R stands for a —CO—X group, wherein X means a halogen atom; or for a —CO—OR$^1$ group, wherein R$^1$ means an unsubstituted or mono- or polysubstituted C$_{2-10}$ aliphatic group, a C$_{3-8}$ alicyclic group, an aromatic C$_{6-14}$ hydrocarbyl group, a C$_1$-C$_8$-alkylamino group or 3-pyridyl methyl, where the substituents of the above aliphatic, alicyclic and aromatic hydrocarbyl groups are halogen, hydroxyl, C$_{6-14}$ aryl, C$_{1-8}$ alkyl, a C$_{1-8}$ alkoxy, a C$_{1-8}$ alkylthio, trifluoromethyl, carboxyl, an alkoxycarbonyl group containing 1 to 8 carbon atoms, nitro or cyano; or for a —CO—NR$^2$R$^3$ group, wherein R$^2$ and R$^3$ are the same or different and stand for a hydrogen atom or a C$_{1-8}$ alkyl group or R$^2$ and R$^3$ form a saturated 5 or 6-member heterocycle together with the adjacent nitrogen atom optionally mono- or polysubstituted by C$_{1-8}$ alkyl and R$^3$ may also represent an amino group when R$^2$ stands for a hydrogen atom; or for a cyano group, as well as their salts.

2. A compound selected from the group consisting of
ethyl 9-nitroapovincamate,
ethyl 11-nitroaapovincamate,
9-nitroapovincaminic acid chloride, 11-nitroapovincaminic acid chloride,
dimethylaminopropyl 11-nitroapovincamate,
dimethylaminopropyl 9-nitroapovincamate,
benzyl 11-nitroapovincamate,
benzyl 9-nitroapovincamate,
3-pyridylmethyl 11-nitroapovincamate,
3-pyridylmethyl 9-nitroapovincamate,
2-hydroxyethyl 9-nitroapovincamate,
2-hydroxyethyl 11-nitroapovincamate,
isobutyl 9-nitroapovincamate,
isobutyl 11-nitroapovincamate,
octyl 9-nitroapovincamate,
octyl 11-nitroapovincamate,
propyl 9-nitroapovincamate,
propyl 11-nitroapovincamate,
9-nitroapovincaminic acid amide,
11-nitroapovincaminic acid amide,
9-nitroapovincaminic acid nitrile,
11-nitroapovincaminic acid nitrile,
9-nitroapovincaminic acid diethylamide, 11-nitroapovincaminic acid diethylamide,
9-nitroapovincaminic acid 4-methylpiperidide,
11-nitroapovincaminic acid 4-methylpiperidide,
phenyl 11-nitroapovincamate,
phenyl 9-nitroapovincamate,
11-nitroapovincaminic acid hydrazide and
9-nitroapovincaminic acid hydrazide,
propargyl 9-nitroapovincaminate,
propargyl 11-nitroapovincaminate,
2'-trifluoroethyl-9-nitroapovincaminate,
2'-trifluoroethyl 11-nitroapovincaminate,
allyl 9-nitroapovincaminate,
allyl 11-nitroapovincaminate,
cyclopentyl 9-nitroapovincaminate,
cyclopentyl 11-nitroapovincaminate, and the hydrochloride of these compounds.

3. A pharmaceutical composition having vasodilating, antispasmolytic, antihypoxic and anti-convulsive effects which comprises an effective amount of a compound of the formula (I) as defined in claim 1 or a pharmaceutically acceptable salt thereof in admixture with a pharmaceutically acceptable carrier.

4. A compound selected from the group consisting of
ethyl 9-nitroapovincamate,
ethyl 11-nitroapovincamate,
9-nitroapovincaminic acid chloride,
11-nitroapovincaminic acid chloride,
dimethylaminopropyl 11-nitroapovincamate,
benzyl 11-nitroapovincamate,
3-pyridylmethyl 11-nitroapovincamate,
2-hydroxyethyl 9-nitroapovincamate,
2-hydroxyethyl 11-nitroapovincamate,
isobutyl 9-nitroapovincamate,
octyl 9-nitroapovincamate,
propyl 9-nitroapovincamate,
9-nitroapovincaminic acid amide,
9-nitroapovincaminic acid nitrile,
11-nitroapovincaminic acid diethylamide,
9-nitroapovincaminic acid 4-methylpiperidide,
phenyl 11-nitroapovincamate,
11-nitroapovincaminic acid hydrazide,
propargyl 9-nitroapovincaminate,
2'-trifluoroethyl-9-nitroapovincaminate,
allyl 9-nitroapovincaminate,
cyclopentyl 9-nitroapovincaminate.

5. A method for the therapeutic treatment of hypoxia comprising administering to an hypoxic animal a pharmaceutical composition as defined in claim 3 to produce an antihypoxic effect.

6. The method of claim 5 wherein said pharmaceutical composition comprises ethyl 9-nitroaprovincamate or ethyl 11-nitroaprovincamate as the active component.

7. The method of claim 5 wherein the composition is administered so as to prevent hypoxic damage.

8. The method of claim 5 wherein the composition is administered so as to increase the tolerance of an animal to hypoxic states.

* * * * *